United States Patent [19]
Peterson

[11] Patent Number: 5,246,454
[45] Date of Patent: Sep. 21, 1993

[54] ENCAPSULATED IMPLANT

[76] Inventor: Robert L. Peterson, 1319 Punahou St., Suite 1070, Honolulu, Hi. 96826

[21] Appl. No.: 733,813
[22] Filed: Jul. 22, 1991
[51] Int. Cl.[5] ............................................. A61F 2/12
[52] U.S. Cl. ........................................... 623/8; 623/7
[58] Field of Search ................................ 623/7, 8, 66

[56] References Cited

U.S. PATENT DOCUMENTS

| | | | |
|---|---|---|---|
| 2,542,619 | 5/1949 | Bernhardt | 623/7 |
| 2,636,182 | 4/1953 | Freedman | 623/7 |
| 4,507,810 | 4/1985 | Bartholdson | 623/8 |
| 4,650,487 | 3/1987 | Chaglassian | 623/8 |
| 4,790,848 | 12/1988 | Cronin | 623/8 |
| 4,955,909 | 9/1990 | Ersek et al. | |
| 4,960,425 | 10/1990 | Yan et al. | |
| 4,963,150 | 10/1990 | Brauman | |
| 4,984,585 | 1/1991 | Austad | |

Primary Examiner—David Isabella
Assistant Examiner—Gina M. Gualtieri
Attorney, Agent, or Firm—James Creighton Wray

[57] ABSTRACT

Surgical implants for human breasts have small, 5-10 cc flat disc-shaped pouches containing saline material. About 20-50 pouches are held within an outer membrane. The encapsulation of the saline solution within the pouches provides an apparent increase of viscosity of saline, and the flat disc shapes provide protection against rupture.

9 Claims, 2 Drawing Sheets

ENCAPSULATED IMPLANT

BACKGROUND OF THE INVENTION

This invention concerns implants for human bodies, and particularly breast implants.

Implants are used to augment or re-shape body portions, or to replace or restore diseased or injured body parts or parts removed by surgery or trauma.

Of particular interest are breast prosthesis or implants which are used to augment, re-shape or replace human breast tissue.

Particularly, breast implants are used for placement between pectoral muscles and breast tissue. The implants can also be placed under pectoral muscles between pectoral muscles and the rib cage. Typically, implants are made of soft fluid impermeable rupture-preventing material such as silicone rubber. Layers of material may be used. The bags may be filled or inflated with fluid materials, usually a gel and more recently a or saline solution. A gel has been preferred because of its ability to match the weight and feel of tissue which the implants are designed to augment, supplant or replace, and because saline implants deflate rapidly if a leak develops.

At the time of this invention, concern with rupturing of the bag or leakage of the gel and its possible effect on long-range health has been expressed. It is believed that the concerns may be unfounded, since the preferred gel is stable and non-reactive with human biological fluids or tissue.

Simple replacement of the gel by saline solution is not satisfactory because saline does not have the weight and feel of the gel and saline solution flows more freely in the implant than the tissue which it replaces. In addition, even a minute crack or hole in the shell leads to rapid deflation of the implant, exposing the patient to the risks and expense of reparation.

Some of the biggest problems with the current saline implants are threefold: They deflate rapidly when the membrane is ruptured. They have a less natural feel than silicone implants. They are prone to compressive capsular formation.

The present invention is directed toward a solution of those problems.

Prior art implant devices may experience contracture, causing unwanted firmness of the implant which is intended to be soft and flexible. That is because scar tissue may tend to surround and may tend to compress the implant. Prior art implant devices have approached the problem by constructing outer surfaces of Teflon and roughening the outer surfaces to redirect scar tissue.

Prior art saline-filled implants are prone to rapid deflation. The present invention solves that problem by encapsulation of the saline.

Prior art saline-filled implants had an unnatural feel. The present design implant, by encapsulating the saline, gives a more viscous feel to the saline, matching the feel of normal breast tissue.

The present invention uses the non-smooth outer surfaces made of the prior art structure and composition to reduce the problem, and also uniquely tends to solve the problem by virtue of a changed inner structure.

SUMMARY OF THE INVENTION

The present invention provides surgical implants for human breasts, which have small, 5-10 cc pouches containing saline material without voids or gas. The small pouches are held within an outer membrane. About 20-50 pouches fill each outer membrane. The encapsulation of the saline solution within the small pouches provides an apparent increase of viscosity of saline. Preferably the small pouches have flat disc shapes, which provide protection against rupture.

A preferred human breast implant comprises a flexible outer membrane containing small individual pouches within the membrane and fluid material sealed within the pouches.

Preferably the fluid with the breast implant pouches is saline solution. The preferred pouches have a generally flat form and round peripheries. Preferably the pouches are loosely positioned within the outer membrane and the pouches fill the membrane.

The encapsulation of the saline in the small pouches effectively increases apparent viscosity of the saline. The preferred pouches are small bags, about 2 to 20 cubic centimeters in volume and preferably about 5 to 10 cubic centimeters in volume. The pouches are formed as a skin around the encapsulated fluid. Encapsulating about 5 to 10 cubic centimeters of saline solution in each pouch increases apparent viscosity of saline, enhances the stability of the implants and provides a more natural feel. The bags are disc-shaped for increasing surface area to volume ratio of the bags and making the bags relatively rupture-proof. From about 40 to 48 disc-shaped bags are held within the outer membrane in a preferred implant.

Problems of the prior art are avoided by modification of the implant to encapsulate the saline according to the present invention. The manufacture of saline implants using encapsulation of saline is one of the objects of the invention.

By encapsulation of the saline into small bags similar to bath oil beads within the implant membrane, rapid deflation is impossible, even with disruption of the outer membrane. Small bags of about 2-20 cc and preferably 5-10 cc are packaged into an outer, larger membrane.

Encapsulation has the additional benefit of increasing the apparent viscosity of the saline. That enhances the stability of the implant, giving it a more natural feel.

Prevention of capsular contracture relies on the same technologies that are currently employed for the silicone prostheses; texturing of the surface.

Saline is an excellent solution for filing the pouches, but other options may be slightly better. One example is Ringer's Lactate. Although saline is slightly hypertonic, the volume involved is small. Saline has the advantage of being extremely stable, non-reactive and inexpensive.

Preferably the small beads are not spherical. Spherical beads might be more easily ruptured. To diminish the problem of rupture, the beads are disc-shaped. That increases their surface area-to-volume ratio and makes them relatively rupture-proof.

A preferred form of the invention uses 5 cc disc/bags, which simplifies sizing of the implants. A 200 cc implant contains 40 discs, a 240 cc implant contains 48 discs, etc.

The advantages of the encapsulated saline implant are many. The implant offers significant advantages in safety and in perceived safety. Leakage of saline within the implant and deflation of individual pouches would be highly unlikely, and perfectly safe. Leaking of saline from a ruptured outer membrane and a few or more than a few pouches would be safe.

The implant is radiographically isodense with saline. That should make mammographic detection of malignancy easier in patients with this implant than in those with silicone implants.

Concerns regarding silicone implants may prove in future years to be unfounded. At the present, however, there is insufficient data to allay the public's fears. Since there is no advantage of silicone implants over encapsulated saline ones, there is no reason to use silicone implants. Conversely, there are significant advantages of the present implants over all current prostheses, and there are compelling safety reasons for preferring them.

These and further and other objects and features of the invention are apparent in the disclosure, which includes the above and ongoing written specification, with the claims and the drawings.

DETAILED DESCRIPTION OF THE DRAWINGS

Figure 1:
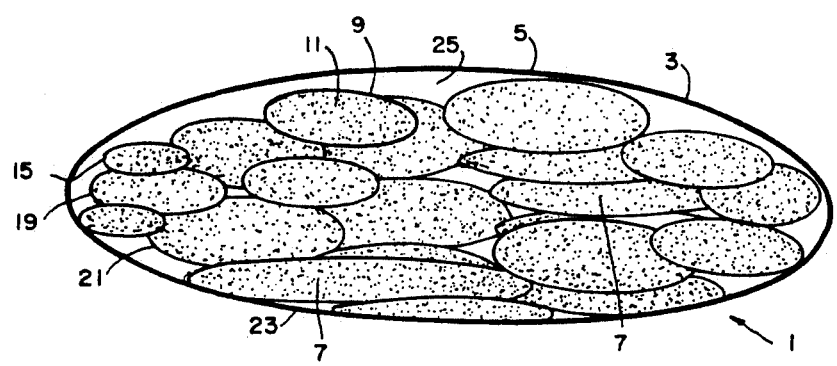
FIG. 1 is a cross-section of one embodiment of an implant outer membrane filled with disc-shaped saline-filled pouches.

Referring to FIG. 1, a preferred breast implant 1 is made with a relatively thick outer membrane 3 which is made of any suitable material, for example silicone rubber. An outer surface 5 may be coated and roughened to redirect scar tissue growth. Within the relatively thick outer membrane are a plurality of small saline-filled pouches 7. Each pouch is made of a relatively thin disc-shaped outer layer 9 and is filled with saline solution 11 or other biologically compatible solution or gel. In one preferred embodiment all discs are of a similar size, holding about 5 cc of solution. In another embodiment, all of the small bags are of an equal size and hold about 10 cc of solution. In another embodiment, as shown in the drawings, the individual bags 7 may be made of varied size such as small bags 15, intermediate bags 19, and larger bags 21. In addition, there may be larger bags 23 which may have an elliptical or elongated shape. It is preferable for the bags to hold between 2 cc and 20 cc of saline solution.

In preferred embodiments, all of the small bags are generally flat so the bags may readily deform upon localized contact or pressure without increasing internal pressure, which might otherwise influence the bags to rupture.

The bags 7 in a preferred arrangement are loosely arranged within the thick outer membrane 3. Alternatively, the bags may be fused, bonded or welded to surfaces of adjacent bags.

In one embodiment, all of the bags are formed with a similar saline solution. In other embodiments of the invention, the bags may be filled with gels or with differing solutions, or with gels of different compositions or physical qualities. The bags may be part-filled with gel and part-filled with fluids which do not dissolve the gel.

In a preferred embodiment, the individual bags 7 are free to move within the outer membrane 3. Alternatively, the bags may be shaped or positioned in such a way as to restrict or prevent their movement within the outer membrane 3. Outer surfaces of the bags may be bonded or welded to the inner surface of the membrane, when freedom of movement of the bags is not desired.

The bags may be interconnected with orifices which permit flow between adjacent bags in groups of two or more.

In a preferred embodiment, surfaces of the bags and an inner surface of the outer membrane are smooth. In an alternate embodiment, surfaces of the bags may be textured, roughened or formed in a non-slip manner to discourage or retard relative movement of the bags. An inner surface of the thick outer membrane 3 may be similarly formed.

In one embodiment of the invention, spaces 25 among the bags and between the bags and the thick outer membrane 3 may be evacuated and refilled with inert biocompatible gas at or below atmospheric pressure or slightly above atmospheric pressure. The space 25 may be filled with saline solution or with a biocompatible gel.

In one form of the invention, the individual bags are made with soft, flexible substances such as silicone rubber with fluid impermeable skins 9.

The disc-shaped bags 7 may be inserted into a preformed outer membrane 3, such as through a slit which is resealed, or the thick outer membrane may be formed after the bags are arranged in a desired number and relationship.

Figure 2:
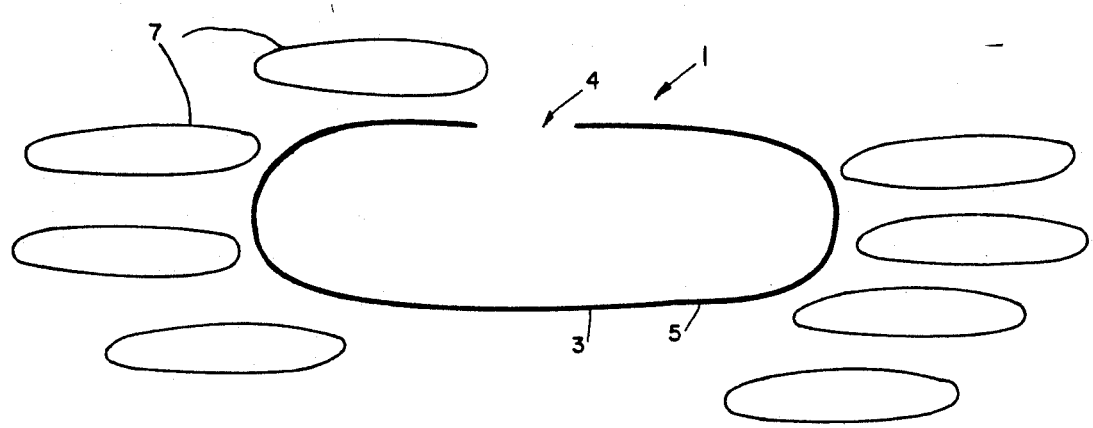
FIG. 2 shows an implant shell and uniform saline packets before assembly.
Figure 3:
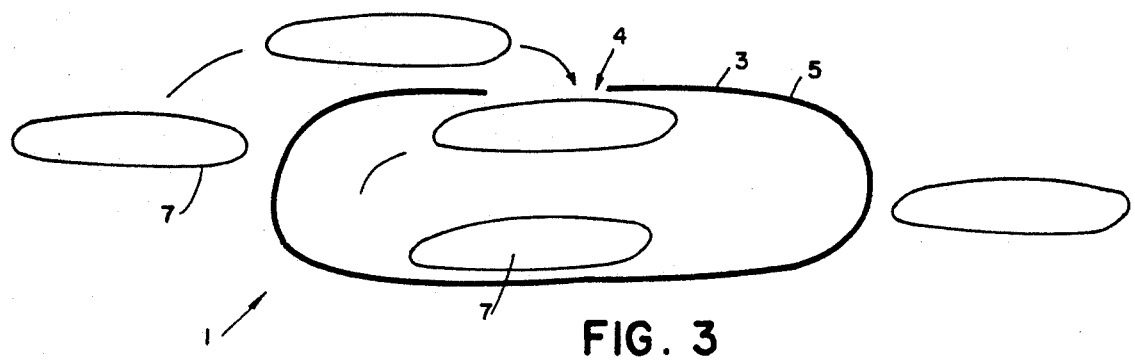
FIG. 3 shows inserting the packets into an open shell before closing.
Figure 4:
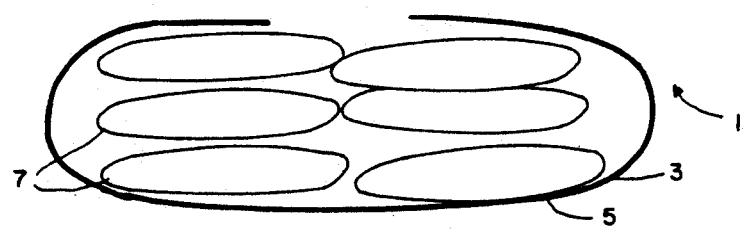
FIG. 4 shows the nested packets with spaces still existing within the shell.

A preferred embodiment of the invention is assembled as shown in FIGS. 2-5. FIG. 2 shows the formed saline packets 7 and shell 3 having opening 4 for insertion of the packets. FIG. 3 shows insertion of the packets 7 and subsequent nesting. In one embodiment, the packets are uniformly constructed 5 cc saline bags which nest within the open shell, FIG. 4, leaving spaces prior to sealing of the shell.

Figure 5:
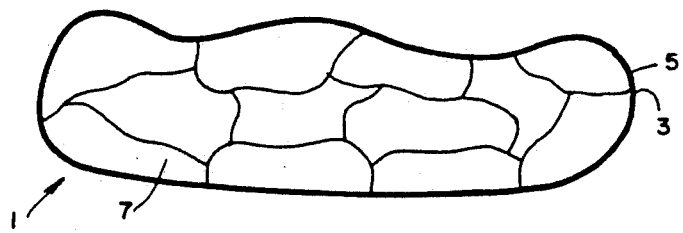
FIG. 5 shows a preferred embodiment of the sealed shell, wherein spaces within have been evacuated.

FIG. 5 shows the sealed shell wherein air spaces have been evacuated, causing the saline packets to be tightly packed within the shell. The shape of the shell, therefore, depends upon forces applied to the implant with less lateral movement allowed because of evacuation of spaces 25 shown in FIG. 1.

The outer container may be net-like or porous so that the small pouches are held in place without a fluid or tissue barrier between the pouches and the surrounding fluid and tissue.

While the invention has been described with reference to specific embodiments, modifications and variations of the invention may be constructed without departing from the scope of the invention, which is defined in the following claims.

I claim:

1. A bio-compatible human breast implant for augmenting, reshaping or replacing human breast tissue, comprising a flexible outer membrane containing a plurality of small individual pouches which are stackably layered within the membrane and fluid material sealed within the pouches, wherein each of the pouches is disc-shaped and has a generally flat form with a height less than a width.

2. The breast implant of claim 1, wherein the fluid in the pouches is saline solution.

3. The breast implant of claim 1 wherein the pouches have round peripheries.

4. The breast implant of claim 1, wherein the pouches are loosely positioned within the outer membrane.

5. The breast implant of claim 4, wherein the pouches fill the membrane.

6. The breast implant of claim 5, wherein the fluid is saline solution and encapsulation of the saline solution in the small pouches effectively increases apparent viscosity of the saline solution in the entire implant.

7. The breast implant of claim 1, wherein the pouches form a skin around the encapsulated fluid.

8. The breast implant of claim 1, wherein each of the pouches is a small bag of about 2 to 20 cubic centimeters in volume, and wherein about 2 to 20 cubic centimeters of saline solution is encapsulated in each pouch for increasing apparent viscosity of saline, and enhancing the feel of the implants and providing a more natural feel, wherein each of the bags is disc-shaped for increasing surface area to volume ratio of the bags and making the bags relatively rupture-proof, and wherein from about 10 to 80 disc-shaped bags are held within the outer membrane.

9. The breast implant of claim 8, wherein about 40 to 48 bags each contain about 5 to 10 cubic centimeters of fluid.

* * * * *